United States Patent [19]
Arpe

[11] 3,932,518
[45] Jan. 13, 1976

[54] METHYLATION OF CYCLOHEXANONE WITH SIMULTANEOUS DEHYDROGENATION

[75] Inventor: Hans-Jürgen Arpe, Fischbach, Taunus, Germany

[73] Assignee: Hoechst Aktiengesellschaft, Frankfurt am Main, Germany

[22] Filed: Nov. 21, 1973

[21] Appl. No.: 417,757

[30] Foreign Application Priority Data
Nov. 24, 1972 Germany............................. 2257675
May 24, 1973 Germany............................. 2326406

[52] U.S. Cl.............. 260/586 R; 252/447; 252/454; 252/455 R; 252/455 Z; 252/457; 252/463; 252/476; 260/588; 260/590 R; 260/592; 260/593 R; 260/621 H
[51] Int. Cl.²......................................... C07C 45/00
[58] Field of Search........ 260/586 R, 590, 591, 592, 260/593 R, 586 A

[56] References Cited
UNITED STATES PATENTS

| | | | |
|---|---|---|---|
| 2,064,254 | 12/1936 | Fuchs et al..................... | 260/593 R |
| 2,549,520 | 4/1951 | Prichard......................... | 260/586 R |
| 2,697,730 | 12/1954 | Mercorney et al.............. | 260/593 R |
| 2,725,400 | 11/1955 | Mercorney et al.............. | 260/593 R |
| 3,047,630 | 7/1962 | Addy et al. ..................... | 260/593 R |
| 3,114,772 | 12/1963 | Lorette et al. .................. | 260/586 R |
| 3,668,255 | 6/1972 | Meuly et al..................... | 260/586 R |
| 3,673,255 | 6/1972 | Etherington et al. ........... | 260/586 R |
| 3,781,307 | 12/1973 | Chabardes et al. ......... | 260/586 R X |

OTHER PUBLICATIONS

Ipatieff et al., "J. Org. Chem.," Vol. 7, pp. 189–198 (1942).

*Primary Examiner*—Norman Morgenstern
*Attorney, Agent, or Firm*—Curtis, Morris & Safford

[57] ABSTRACT

Catalytic process for alkylating ketones carrying at least one methyl or methylene group in α-position to the carbonyl group by reacting them with primary alcohols in the presence of copper and/or silver catalysts.

2 Claims, No Drawings

METHYLATION OF CYCLOHEXANONE WITH SIMULTANEOUS DEHYDROGENATION

The present invention relates to a catalytic process for alkylating ketones carrying at least one methyl or methylene group in α-position to the carbonyl group.

Up to now a simple and economic process for alkylating ketones, i.e. for the synthesis of higher ketones from simple unbranched ketones, has not been proposed.

It is known, however, to alkylate ketones with alkyl halides, preferably the bromides or iodides, but in most cases stoichiometric amounts of alkaline substances, such as alkali metals, alkali metal alcoholates, alkali metal hydroxides or alkali metal amides, must be used, which in part necessitate the use of expensive solvents, for example alkali metal amide in liquid $NH_3$. It has also been proposed to alkylate ketones by using, additionally ammonia, amines or quaternary ammonium bases besides alkali metal compounds, mostly alkali metal hydroxides to neutralize the hydrogen halide formed in the alkylation with alkyl halides. The obvious drawback of this type of alkylation is the formation of stoichiometric amounts of alkali metal halides or ammonium halides or amine hydrohalides, from which the halogen portion and the free base cannot be recovered or can be recovered with difficulty only. Hence, problems arise how to utilize these by-products or to eliminate them without environmental pollution.

The present invention provides a catalytic process for alkylating ketones carrying at least one methyl or methylene group in α-position to the carbonyl group, which process is characterized by good selectivities and permits the production of higher ketones in simple and economic manner.

The object of the invention is a process for alkylating ketones in α-position to the carbonyl group, which comprises reacting a ketone of the formula $R^1CO$—$CH_2$—$R^2$ in which $R^1$ and $R^2$ represent alkyl, cycloalkyl or alkenyl, each having up to 12 carbon atoms, or aryl, $R^2$ may also stand for hydrogen and $R^1$ and $R^2$ together with the —$CH_2$—$CO$— group may be part of a cycloaliphatic ring having up to 12 carbon atoms with a primary alcohol of the formula $R^3CH_2OH$ in which $R^3$ is hydrogen, alkyl, cycloalkyl or alkenyl having up to 6 carbon atoms, at a temperature of from 100° to 500°C, preferably 200° to 400°C, in the gaseous or liquid phase in the presence of a catalyst containing metallic copper and/or silver.

It is surprising that the alkyl halides used in known alkylation reactions can be replaced by the cheaper alcohols which can be activated by a catalyst in such a manner that the alkylation of the ketones takes place with good yields and with a high reaction speed. The use of primary alcohols for the alkylation of ketones has not been proposed so far.

When a methyl ketone is monoalkylated in the methyl group according to the process of the invention a straight chain ketone is obtained, for example using acetone and methanol or ethanol, methylethyl or methyl-n-propyl ketone is obtained. When the ketone contains an α-methylene group, the ketone obtained by the alkylation has an α-branching. With ketone having two methylene groups capable of being alkylated, the monoalkylation can yield, depending on the reaction conditions, mixtures of different composition of two new ketones, for example methyl-ethyl ketone and methanol yield mixtures of diethyl and methyl-isopropyl ketone, which may be further alkylated to give ethyl-isopropyl ketone and diisopropyl ketone.

Suitable ketones which can be alkylated with primary alcohols according to the invention are, for example acetone, methylethyl ketone, diethyl ketone, methylpropyl ketone, methylisopropyl ketone, methylisobutyl ketone, methyl-t-butyl ketone, methylhexyl ketone, methylcyclohexyl ketone; olefinic ketones such as mesityl oxide; alicyclic ketones such as cyclopentanone, cyclohexanone, cycloheptanone, cyclododecanone and their alkyl derivatives, camphor, acetophenone, methylbenzyl ketone, ethylphenyl ketone, as well as phenyl ketones substituted in the benzene nucleus.

Primary alcohols suitable as alkylating agents are, for example, methanol, ethanol, propanol, isobutanol and allyl alcohol.

The starting materials for the alkylating reaction need not have a high purity. Ketone mixtures composed of a ketone and its alkylation products may be used as well as alcohols containing the corresponding aldehyde as impurity. As water is a by-product of the alkylation, the reaction components need not be anhydrous.

The proportion of alcohol to ketone in the process according to the invention may vary within wide limits. To obtain a high yield of monoalkylated ketones the alcohol is preferably used in deficiency up to a proportion of at most 1 : 1. If, however, the production of higher alkylated ketones is desired, a ratio of alcohol to ketone greater than 1 : 1 will preferably be chosen, for example 2 : 1 to 20 : 1. In the latter process with continuous operation, the ketones of low degree of alkylation can be recycled into the reaction, optionally after separation of the higher alkylated ketones.

The catalyst to be used according to the invention for the production of the alkylated ketones contains metallic copper and/or silver, supported or not on a carrier.

The finely divided reactive copper and silver metal necessary for the reaction can be prepared in known manner from their compounds, for example the oxides, hydroxides, carbonates, nitrates, acetates, oxalates or other organic compounds or complex compounds. The said compounds or complex compounds are reacted to yield the metal with reducing gases, for example $H_2$ or CO, or with vapors, for example of methanol or ethanol, or of the reaction components of the process of the invention. When the carbonates, nitrates, acetates, or oxalates are used a thermal decomposition at elevated temperatures, for example at 500°C, to give the oxides, can be performed prior to the reduction.

Alternatively, alloys can be used for making the catalysts of the invention, for example a copper/aluminum alloy. By dissolving the aluminum with alkali metal hydroxide solution active catalysts of the Raney type are obtained.

When a carrier is used it is impregnated with a solution of the aforesaid copper and/or silver compounds, for example an aqueous solution of copper and/or silver nitrate or acetate, and the salts are reduced, or prior to the reduction they are transformed into the hydroxides by introducing the impregnated carrier material into aqueous alkali metal hydroxide solution. After elimination of foreign ions by a washing process, the hydroxides are reduced to the metals in a manner analogous to that described above.

Suitable carrier materials are, for example, aluminum oxide, aluminum silicate, magnesium silicate, silica gel, carbon, zeolites and pumice.

The carrier can also be precipitated simultaneously with the copper and/or silver compound in an aqueous solution of copper and/or silver salt and, for example, an aluminum or silicium compound. Commercially available catalyst materials may be used, too, for making the catalysts of the invention. Industrial copper or silver catalysts may be used, possibly after reduction to the metals.

The concentration of the copper and/or silver on the carrier material can vary within wide limits. In many cases a concentration of from 0.5 to 25 % by weight is effective. Good results can also be obtained with a concentration above 25 % by weight.

When a copper and/or silver catalyst is used without carrier material very finely divided material may be transformed into coarser grains, for example by compression.

Higher yields of alkylated ketones are obtained by using a copper and/or silver catalyst additionally containing one or more basic components, for example oxides, hydroxides, or alcoholates of alkali metals, alkaline earth metals or rare earth metals. Other metals, the oxides, hydroxides or alcoholates of which have a basic reaction, such as zinc, cadmium or lead, are likewise suitable as promotors. When alcoholates are used, those corresponding to the alcoholic reaction component should be used. Other alcoholates may, of course, also be used without any disadvantage occurring.

The promotors can be applied to the carrier as such together with the copper and/or silver compound or the carrier can be impregnated with the promoter solution after reduction of the copper and/or silver compound to the metal. The carrier can also be impregnated with carbonates, bicarbonates, acetates, oxalates, or nitrates of alkali metals, alkaline earth metals, and/or rare earth metals, which are then transformed into the oxides, hydroxides or alcoholates during the thermal treatment, the reduction, or in the course of the reaction according to the invention.

When the reaction is carried out in the liquid phase the promotor can be added to the reaction mixture also in the form of a solution, suitably in one of the reaction components, for example an alkali metal oxide, hydroxide or alcoholate dissolved in an alcohol.

In the alkylation according to the invention the oxides, hydroxides, or alcoholates of the following metals may be used: lithium, sodium, potassium, rubidium, cesium, magnesium, calcium, lead, or rare earth metals, either alone or in admixture with one another. A suitable mixture of rare earth metals is, for example, the commercially available didymium.

The amount of oxides, hydroxides or alcoholates applied to the carrier can vary within wide limits, preferably in the range of from 0.01 to 10 % by weight, calculated on the metal catalyst. Higher concentrations being likewise possible.

The alkylation according to the invention is carried out at a temperature in the range of from 100° to 500°C, preferably 200° to 400°C. A mixture of the vaporous reaction components ketone and alcohol, optionally with the addition of an inert diluent, is passed in the gaseous phase, either alone or together with inert gases such as nitrogen or argon, over the catalyst, which is either in a fixed bed or in a fluidized bed created by the vaporous reactants. The residence time is in the range of from 0.1 to 100 seconds, preferably 1 to 20 seconds.

The reaction is performed at atmospheric pressure. The use of super-atmospheric pressure is, however, also possible.

After condensation of the reaction products, the constituents are separated in known manner and the alkylated ketones are obtained, for example, by distillation or extraction. Unreacted starting products may be passed again over the catalyst.

Alternatively, the alkylation can be carried out in the liquid phase. In order to reach a temperature necessary for a sufficient reaction speed, it is suitable to use ketones or alcohols which boil below said temperature in a closed apparatus, for example an autoclave. In this case the catalyst is added in finely divided form in an amount of from 5 to 30 % by weight, calculated on the feedstock. Good yields are likewise obtained with larger or smaller catalyst amounts.

After separation of the catalyst by filtration, the reaction product is separated, for example by distillation, into the reaction products and starting components, which can be reacted again in the presence of the catalyst.

It has been found that the course of the methylation of cyclohexanone is dependent on whether the reaction is carried out in the liquid or in the gaseous phase, on the residence time and on the reaction temperature.

In this methylation the choice of the reaction phase and the reaction temperature decisively influences the type of reaction products obtained and their quantitative composition.

When the methylation of cyclohexanone with methanol is carried out in the gaseous phase at a temperature above 250°C, preferably in the range of from 280° to 400°C with a residence time of less than 60 seconds, a dehydrogenation simultaneously takes place.

As disclosed in the comparative examples, unsaturated methylation products of cyclohexanone may form in small amounts in the liquid phase with a short residence time and at higher temperature under pressure. The yields in the gaseous phase are, however, much higher.

The dehydrogenation simultaneously taking place can be further promoted by the presence of oxygen containing gases which are passed over the catalyst together with cyclohexanone and methanol. In the dehydrogenating methylation the cyclohexanone forms, besides 2-methyl- and 2,6-dimethyl-cyclohexanone, which can also be obtained in the liquid phase, mainly the unsaturated compounds 2-methylcyclohexene-2-one and 2,6-dimethylcyclohexene-2-one, as well as 2,6-dimethylphenol and a little 2-methylphenol and hexamethylbenzene

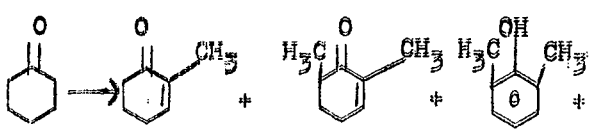

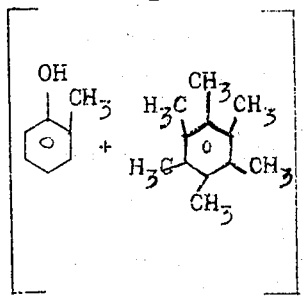

As α,β-unsaturated ketones, methyl and dimethylcyclohexenone are valuable intermediates for the synthesis of dyestuffs, plant protecting agents and pharmaceutically active ingredients. 2,6-Dimethylphenol or 2,6-xylenol is the starting component for the manufacture of polyphenylene oxides having good thermostability, stability to acids and bases, as well as good dielectric properties.

To obtain a high yield of 2-methylcyclohexene-2-one methanol is preferably used in deficiency, up to at most the molar proportion with respect to cyclohexanone. When, however, 2,6-dimethylcyclohexene-2-one or 2,6-xylenol shall be produced, the proportion of methanol to cyclohexanone is preferably greater than 1 : 1, for example 2 : 1 to 20 : 1.

To perform the methylation with simultaneous dehydrogenation a vaporous mixture consisting of methanol and cyclohexanone, optionally with the addition of an oxygen containing gas, preferably air, is passed over the catalyst, which is either in a fixed bed or whirled up to a fluidized bed by the vaporous methanol/cyclohexanone mixture.

The reaction is mostly carried out at atmospheric pressure. It is likewise possible to operate at elevated pressure or reduced pressure. After condensation, the reaction products are separated in known manner, for example by distillation or extraction in liquid phase. Unreacted starting products can be recycled into the reaction.

The alkylation process according to the invention permits to prepare in simple and economic manner a series of alkylated ketones which can otherwise by obtained by complicated processes and often by indirect methods with numerous reaction stages only.

The parameters used in the following examples for the used ketone and the alkylated alkyl ketone obtained are defined as follows:

The conversion of a ketone is the molar portion in percent of the reacted ketone, calculated on the amount of ketone used.

The selectivity of an alkyl ketone is its molar portion in percent, calculated on the reacted ketone.

The yield of an alkyl ketone is its molar portion in percent, calculated on the amount of ketone used.

The following examples illustrate the invention.

EXAMPLE 1

100 ml $SiO_2$ (pore volume 0.8 g $H_2O$/ml, surface 160–180 $m^2$/g) were impregnated with an aqueous solution of 3.3 g $AgNO_3$, the impregnated carrier material was dried and stirred into 100 ml of 2 % aqueous potassium hydroxide solution. The preliminary catalyst obtained was filtered off and washed until it was free from nitrate. It was then dried at 200°C under about 50 torr and reduced at 400°C with hydrogen diluted with nitrogen.

In a glass reactor having a length of 320 mm and a diameter of 21 mm the catalyst was heated by means of two electric furnaces to a constant temperature which was regulated inside of the reactor with a displaceable thermocouple. The upper third of the reactor had the function of an evaporator, the remaining two thirds constituted the reaction zone proper. To collect the reaction products, two traps were used cooled to about −70°C with dry ice/butanol.

After a starting period generally of 2 hours to obtain constant operating conditions, the reaction was performed over a prolonged period of time.

With the aid of an external standard mixture the reaction products and unreacted feedstock were analyzed in the combined condensates by gas chromatography. In most cases the reaction mixture was then separated by distillation.

By means of a pump 30 ml/h of a 2 : 1 molar mixture of acetone and methanol were passed at atmospheric pressure over the catalyst heated to 400° – 410°C. With an acetone conversion of 19.0 mole % the selectivity of methylethyl ketone was 81.3 mole %, i.e. the yield was 15.5 mole %.

EXAMPLE 2

100 ml $SiO_2$ (pore volume 0.8 g $H_2O$/ml, surface 160 – 180 $m^2$/g) were impregnated with an aqueous solution of 4.8 g $Cu(NO_3)_2.3 H_2O$ and stirred into 100 ml of 4.5 % aqueous potassium hydroxide solution. After washing, drying and reducing with $H_2$ as described in Example 1, the catalyst was filled into the reactor as described in said example. 15 ml/h of a 2 : 1 molar mixture of acetone and methanol were passed over the catalyst heated to 290°–300°C. 23.5 mole % of methylethyl ketone were obtained.

EXAMPLE 3

100 ml $SiO_2$ (pore volume 0.8 g $H_2O$/ml, surface 160–180 $m^2$/g) were impregnated with an aqueous solution of 4.8 g $Cu(NO_3)_2$. 3 $H_2O$ and a solution of 1.05 g $Di_2O_3$ (a product of Pechiney-St.Gobain, France, consisting of a mixture of the oxides of lanthanium, cerium, praseodymium, neodymium, and small amounts of samarium, gadolinium, ytterbium and others). The impregnated carrier material was stirred into 150 ml of 4.5 % aqueous potassium hydroxide solution. After washing, drying and reducing with $H_2$ as in Example 1, the catalyst was filled into the reactor used in the said example. 15 ml/h of an equimolar mixture of acetophenone and methanol were passed per hour over the catalyst heated to 300°C.

With an acetophenone conversion of 87.5 mole % the selectivities were 69.6 mole % of ethylphenyl ketone and 21.6 mole % of isopropylphenyl ketone, i.e. the yields of the two compounds were 60.9 mole % and 18.9 mole %, respectively.

EXAMPLE 4

15 ml/h of an equimolar mixture of ethanol and acetone were passed at 300°C over a catalyst prepared and composed as described in Example 3. Methylpropyl ketone was obtained in a yield of 16.0 mole %.

EXAMPLE 5

15 ml/h of an equimolar mixture of allyl alcohol and acetone were passed at 300°C over a catalyst prepared and composed as described in Example 3. 4.6 Mole % of methylbutenyl ketone were obtained.

EXAMPLES 6 TO 12

100 ml γ-Al$_2$O$_3$ (pore volume 0.45 – 0.5 g H$_2$O/ml, surface 66 m$^2$/g) were impregnated with an aqueous solution of 4.8 g Cu(NO$_3$)$_2$. 3 H$_2$O and the impregnated material was stirred into 100 ml of a 4.5 % aqueous potassium hydroxide solution. After washing out the nitrate and potassium ions, the preliminary catalyst was dried and reduced at 400°C with hydrogen diluted with nitrogen. The reduced Cu/Al$_2$O$_3$ catalyst was then impregnated with an aqueous solution of different promotor salts, defined in the following table, in an amount corresponding to 6.25 milliatoms of metal, the impregnated catalyst was dried and used in the reactor described in Example 1 to alkylate acetone with methanol. With the use of 15 ml/hour of a mixture of methanol and acetone in different molar proportions as indicated in the table and 1.8 l/h of nitrogen, the results listed in the table were obtained.

EXAMPLE 13

15 ml/h of a 3 : 1 molar mixture of methanol and methylethyl ketone and 1.8 l/h of nitrogen were passed at 300°C over a catalyst prepared and composed as in Example 6. With a conversion of methylethyl ketone of 77.3 mole % the following yields of methylated methylethyl ketones were obtained: 23.0 mole % of ethylisopropyl ketone, 22.1 mole % of methylisopropyl ketone, 14.6 mole % of diethyl ketone, and 3.3 mole % of diisopropyl ketone, corresponding to selectivities of 29.8 mole %, 28.6 mole %, 18.9 mole % and 4.3 mole %, respectively.

EXAMPLE 14

A commercial copper catalyst containing 26 % by weight of copper as oxide on magnesium silicate was reduced with hydrogen. 100 ml of the catalyst were impregnated with aqueous potassium hydroxide solution containing 0.35 g KOH, and dried.

In a 2 liter VA shaking autoclave 3 moles of cyclohexanone, 6 moles of methanol and 10 g of the described, finely ground catalyst were heated to 250° – 260°C while shaking under a pressure of 5 atmospheres of nitrogen measured at 20°C and kept at the high temperature for 11 hours.

The cooled reaction product was fractionated by distillation. Besides unreacted methanol and cyclohexanone, 0.9 mole = 30 mole % 2-methylcyclohexanone and 0.25 mole = 8.3 mole % dimethylcyclohexanone, calculated on the cyclohexanone used, could be isolated. Small amounts of cyclohexanol and 2-methylcyclohexanol were formed as by-products.

EXAMPLE 15

In a reactor analogous to that described in Example 1, 30 ml/h of a mixture of methanol and cyclododecanone in a molar proportion of 2 : 1 were passed over 100 ml of a catalyst prepared and composed as specified in Example 7 and heated to 300°C. With a conversion of cyclododecanone of 85.3 mole % 2-methyl-cyclododecanone and 2.12-dimethylcyclododecanone were obtained with selectivities of 58.2 and 39.8 mole %, respectively.

EXAMPLE 16

100 ml γ-Al$_2$O$_3$ (pore volume 0.5 – 0.6 ml/g, surface 70 – 120 m$^2$/g) were impregnated in two stages with acetic acid solutions, with intermediate drying in a water jet vacuum, first of 4.0 g Cu(OAc)$_2$. 2 H$_2$O and then of 1.05 g Di$_2$O$_3$ (as defined in Example 3). After drying, the impregnated catalyst was treated with hydrogen (about 3 liters per hour) for 2 hours at 200°C and for another 2 hours at 300°C.

In a glass reactor having a length of 320 mm and a diameter of 21 mm the catalyst was heated to 300°C by two electric furnaces. By means of a pump 30 ml/h of a mixture of methanol and cyclohexanone in a molar proportion of 2 : 1 were passed over the catalyst. The reaction products were collected in two traps cooled to −70°C.

After preliminary period of generally 2 hours to obtain constant operating conditions, the reaction was continued for a prolonged period of time and repeatedly using the same catalyst.

With the aid of an external standard the reaction products and unreacted starting products were analyzed by gas chromatography. The mean analysis values of several runs were determined.

With a cyclohexanone conversion of 95 mole %, the selectivities were 37 mole % of 2-methylcyclohexanone, 24 mole % of 2-methylcyclohexene-2-one, 24 mole % of 2,6-dimethylcyclohexene-2-one, 6 mole % of 2,6-xylenol and 2 mole % of 2,6-dimethylcyclohexanone. Hexamethylbenzene could also be detected.

The total yield of saturated and unsaturated methylation products amounted to 88.4 mole %. The molar proportion of unsaturated to saturated methylation products was about 1.4 to 1 with an average residence time of about 20 seconds.

EXAMPLE 17

Cyclohexanone and methanol were reacted at 360°C and 360 torr in the presence of the catalyst and under the conditions as described in Example 16. With a

| Ex. | promotor metal | molar proportion methanol : acetone | temp. °C | conversion mole % acetone | MEK | MIPK | Yield mole% DEK | EIPK | DIPK |
|---|---|---|---|---|---|---|---|---|---|
| 6 | K | 2 : 1 | 300 | 72.5 | 25.4 | 14.1 | 10.9 | 15.7 | 1 |
| 7 | Di | 4 : 1 | 280 | 91.0 | 12.3 | 16.9 | 6.4 | 29.3 | 18.0 |
| 8 | Li | 4 : 1 | 300 | 20.0 | 5.9 | 3.2 | 2.8 | 3.9 | 1.2 |
| 9 | Cs | 4 : 1 | 300 | 29.3 | 8.9 | 4.4 | 5.1 | 4.3 | 1.4 |
| 10 | Mg | 4 : 1 | 300 | 37.5 | 14.8 | 6.2 | 6.1 | 6.3 | — |
| 11 | Pb | 4 : 1 | 300 | 93.5 | 8.0 | 8.0 | 3.0 | 10.3 | 4.9 |
| 12 | — | 4 : 1 | 300 | 42.2 | 3.5 | — | — | — | — |

MEK = methylethyl ketone
MIPK = methylisopropyl ketone
DEK = diethyl ketone
EIPK = ethylisopropyl ketone
DIPK = diisopropyl ketone conversion of cyclohexanone of 85.5 mole % the proportion of unsaturated to saturated methylation compounds of cyclohexanone was 4.0 to 1, the average residence time was about 9 seconds.

EXAMPLE 18

In a metal reactor containing 1.1 l of catalyst prepared and composed as described in Example 16, 620 ml/h of a molar mixture of methanol and cyclohexanone were reacted at 300°C at atmospheric pressure while introducing 40 l/h of nitrogen.

With a conversion of cyclohexanone of 40.1 mole % and a residence time of 5.6 seconds unsaturated and saturated methylation products of cyclohexanone were obtained in a molar proportion of 2.2 to 1. When the reaction components were passed over the catalyst together with 40 l/hour of air, instead of nitrogen, at a temperature of 290° to 300°C, the molar proportion of unsaturated to saturated methylation products of cyclohexanone rose to 2.7 to 1.

EXAMPLE 19 (comparative example)

In a 1 liter autoclave 3 moles of cyclohexanone and 6 moles of methanol were stirred for 8 hours at 250° – 260°C with 10 g of finely ground catalyst prepared and composed as described in Example 16. With a conversion of 38.7 mole % of cyclohexanone practically no unsaturated methylation products were obtained besides 2-methyl- and 2,6-dimethylcyclohexanone.

EXAMPLE 20 (comparative example)

The methylation was carried out as described in Example 19 for 4 hours at 300°C while stirring, whereby a conversion of cyclohexanone of 60.0 mole % was obtained. Besides the saturated methyl and dimethyl derivatives only traces of unsaturated compounds were detected by gas chromatographic analysis.

What is claimed is:

1. A process for methylating cyclohexanone in α-position to the carbonyl group with simultaneous dehydrogenation in the gaseous phase in the presence of a catalyst consisting essentially of metallic copper supported on a carrier which comprises reacting cyclohexanone with methanol at a temperature from above 250° to 500°C with a residence time of less than 60 seconds and wherein the copper content of the catalyst is from 0.5 to 25 % by weight and the catalyst contains, as a promoter, oxides, hydroxides or alcoholates of potassium, didymium or mixtures of same in an amount from 0.01 to 10 % by weight, based on the copper catalyst.

2. The process as defined in claim 1, wherein the carrier is aluminum oxide, aluminum silicate, magnesium silicate, silica gel, carbon, zeolites and pumice.

* * * * *